United States Patent [19]

Lim et al.

[11] Patent Number: 5,107,121
[45] Date of Patent: Apr. 21, 1992

[54] GANTRY AND PALLET ASSEMBLY USED IN NUCLEAR IMAGING

[75] Inventors: Chun B. Lim, Solon; Rick W. Walker, Kent; Robert E. Sobin, Cleveland; Carlos D. Pinkstaff, Twinsburg, all of Ohio

[73] Assignee: Trionix Research Laboratory, Inc., Twinsburg, Ohio

[21] Appl. No.: 679,173

[22] Filed: Mar. 26, 1991

Related U.S. Application Data

[63] Continuation of Ser. No. 428,188, Oct. 27, 1989, abandoned.

[51] Int. Cl.$^5$ ............................................. G01T 1/166
[52] U.S. Cl. ........................... 250/363.05; 250/363.04; 250/363.08
[58] Field of Search .................. 250/363.05, 363.08, 250/363.04; 378/209

[56] References Cited

U.S. PATENT DOCUMENTS

| | | |
|---|---|---|
| 3,082,322 | 2/1963 | Koerner et al. . |
| 3,431,413 | 3/1969 | Anderson et al. ............. 250/363.02 |
| 3,432,660 | 3/1969 | Anger ........................... 250/363.04 |
| 4,057,727 | 11/1977 | Muehllehner et al. . |
| 4,064,441 | 12/1977 | Casale . |
| 4,105,923 | 8/1978 | Hynes, Jr. . |
| 4,131,802 | 12/1978 | Braden et al. . |
| 4,472,822 | 9/1984 | Swift ..................................... 378/146 |
| 4,523,091 | 6/1985 | Persyk . |
| 4,645,933 | 2/1987 | Gambini et al. . |
| 4,649,277 | 2/1987 | Terra et al. . |
| 4,651,007 | 3/1987 | Perusek et al. ..................... 250/363.08 |
| 4,652,759 | 2/1987 | Platz . |

OTHER PUBLICATIONS

United States Statutory Invention Registration; Bennett et al.; Reg. No.: H12; Published Jan. 7, 1986; Nuclear Medicine Imaging System.
Advertisements: The Journal of Nuclear Medicine, May, 1989.
Article: Product Comparison System; Gantries, Nuclear Imaging, Jun. 1985.

*Primary Examiner*—Carolyn E. Fields
*Assistant Examiner*—Drew A. Dunn
*Attorney, Agent, or Firm*—Pearne, Gordon, McCoy & Granger

[57] ABSTRACT

A gantry and pallet assembly using scintillation cameras to acquire data emitted from radiopharmaceuticals previously introduced into a patient. The radiopharmaceuticals accumulate in a predetermined region of interest within the patient. The gantry can perform both whole body and single photon emission computed tomograph (SPECT) scans. The gantry has two scintillation cameras mounted in a diametrically opposed manner on and in close proximity to a rotation ring. Each camera can be radially translated relative to the rotation ring simultaneously with the rotation of the rotation ring. The gantry is capable of being translated along a pair of translation tracks so that a pallet upon which a patient lies passes therethrough. The pallet assembly has a storage carriage which supports a substantially rectangular flat pallet upon a slidable frame, and a curved pallet upon an extension assembly. The storage carriage can be slid away from the gantry or close to the gantry. When the storage carriage is close to the gantry either pallet can be easily transferred to a vertically adjustable pallet support used during scanning procedures.

33 Claims, 7 Drawing Sheets

GANTRY AND PALLET ASSEMBLY USED IN NUCLEAR IMAGING

This is a continuation of application Ser. No. 07/428,188, filed Oct. 27, 1989 now abandoned.

BACKGROUND OF THE INVENTION

This invention relates to apparatus used in nuclear imaging and more particularly to a gantry and pallet assembly having at least one scintillation camera for conducting whole body or single photon emission computed tomography (SPECT) scans.

Medical technology has developed methods and apparatus which harness radiopharmaceuticals to provide images of a preselected region of the human body that has been made temporarily radioactive. The radiopharmaceutical introduced into the human body selectively accumulates within the region of interest. The radiation emitted by the radiopharmaceutical is detected by one or more scintillation cameras which are used to map the distribution of the radioactively tagged pharmaceuticals. The scintillation camera collects data representative of the radiation emitted by the radiopharmaceutical; the collected data is then used to reconstruct images corresponding to selected transverse planes through the region of interest as shown in U.S. Pat. No. 4,057,727 issued to Muehllehner et al. on Nov. 8, 1977 which is hereby specifically incorporated by reference.

Conventional images have an inherent limitation in that underlying and overlying radioactivity distributions are often superimposed upon the region of interest resulting in images having poor contrast. SPECT imaging eliminates this problem by obtaining multiple views about the patient and using appropriate computer software to generate images of the cross-sectional slices of the region of interest. This is accomplished by either continuously or incrementally rotating at least one scintillation camera around a patient while maintaining the camera close to the patient's body and substantially perpendicular to that region of the patient's body from which data is being collected. For example, as many as 360 views could be obtained if the scintillation camera was incrementally rotated one degree at a time to acquire a complete data set. It is common to rotate the cameras in increments of three degrees resulting in 120 acquisition points. Incremental rotation requires that the scintillation camera be held stationary at each incremental position while data collection takes place.

For more rapid data collection, the scintillation camera can be continuously rotated about the patient and data collected in separate images corresponding to preselected angular increments. This method is not as accurate as incremental rotation for detailed examinations.

When diagnostic rotational SPECT scanning is performed the patient lies on an arcuate narrow table, customarily known as a pallet, which conforms to the patient's body so the detectors can get as close to the patient as possible. Whole body scanning does not require camera head rotation but does require that the detector be translated over the patient's body in linear fashion. It is important that a detector passing above the patient lying on his or her back follows the contour of the patient's body thereby staying close to it. Because no rotation is required the patient lies on a pallet which is wider than the one used for SPECT scanning thereby providing more comfort to the patient. Moreover, the pallet should be flat so a detector passing underneath the patient can get as close to the patient's body as is needed for that particular scan.

Additionally, when conducting a rotational SPECT scan, the amount of time needed to conduct the scan decreases with the number of detectors used. Thus, it may be cost effective and easier on the patient to use two or three detector heads instead of just one when performing a scan.

Rotational SPECT imaging can be performed over any part of a patient's body. Thus, it is necessary to orient the scintillation camera or cameras relative to a pallet so they can be rotated around the region of interest. Additionally, present diagnostic procedures are such that it is economically and practically advantageous to utilize imaging apparatus capable of performing both rotational SPECT scanning and whole body scanning. Thus, the scintillation cameras must be able to translate the length of a patients body as well as rotate around it any point along its axis.

In one commercially available system, the Siemens Rota Camera, a gantry is provided having a through hole of sufficient size to allow a patient supported on a pallet to pass at least part way therethrough. The through hole has a rotation ring mounted therein with two diametrically arranged detectors connected thereto a distance away from the rotation ring. The detectors are capable of being rotated in a plane perpendicular to the longitudinal axis of the through hole. The gantry has arranged therewith an automatically driven bed which can be longitudinally translated through the through hole to conduct a whole body scan. One disadvantage with this arrangement is that vibrations occur within the counter-balanced arms supporting the detectors during rotational SPECT scanning resulting in the acquisition of inaccurate data.

At least one other commercially available gantry, the Elscint Apex 415 ECT, employs concepts similar to the gantry just described including having the detectors mounted a distance away from the rotation ring. A common problem resulting from these designs is that vibrations occur during rotation due to the detectors being located such a distance from the rotation ring. Additionally, for the detectors to translate the length of a patient's body an overly long translation track must be provided.

Another commercially available nuclear imaging apparatus is disclosed in U.S. Pat. No. 4,645,933 issued on Feb. 24, 1987 to Gambini, et. al. which is hereby specifically incorporated by reference. Gambini discloses a medical diagnostic system using the principles of nuclear medicine including a gantry having a detector pivotally supported by a pair of parallel support arms which are pivotally mounted to a detector support section. The support arms are weighted at the end opposite the detector for tilting rotation of the detector about an axis parallel to the arm pivot axis. One disadvantage of this configuration is that it is difficult to obtain a precise orbital rotation of the detector around a patient during an ECT or rotational SPECT scan. Also, the length of the weighted arms contributes to the creation of vibrations during rotation or translation of the detector which can result in the acquisition of inaccurate data.

One manufacturer, ADAC, mitigated the effects of vibrations occuring during rotation or translation of the detector with their Genesys system by introducing a second ring coaxial with a first ring and rotationally mounting one detector therebetween. This approach reduces erroneous data acquisition by stemming vibrations but is limited in that it is not readily adaptable for use with more than one detector because of the location of the pallet upon which a patient lies during scanning. Furthermore, it is not practically possible to have a scan performed while standing or sitting. The location of the pallet inhibits performance of scans requiring the patient to be in a position other than supine.

SUMMARY OF THE INVENTION

Accordingly, the present invention provides a gantry having two diametrically disposed detectors mounted on and in close proximity to a single rotation ring. The rotation ring can be rotated around a patient thereby acquiring data used for rotational SPECT scanning. The ring can also be laterally translated thereby conducting a whole body scan. A pallet for each type of scan is provided upon which a patient lies. The pallet is supportable at each end by a supporting means and is positioned so that it passes through the rotation ring when translated. The position of the pallet makes it easily accessible for a patient getting onto or off of it.

It is a further feature of the invention to provide a substantially rectangular pallet used for whole body scanning and a pallet assembly for storing and moving the pallet. The pallet assembly has means for supporting the pallet at each end to immobilize it during scans. The pallet assembly also has a storage carriage made of a base having a frame pivotally mounted a distance above it. The frame has an extendable section upon which the pallet is supported. The storage carriage can be moved between a position close to the gantry and a position away from the gantry where it won't interfere with scanning procedures. When the storage carriage is close to the gantry the extendable section of the frame can be moved to a position where the pallet is over the pallet supporting means.

It is still a further feature of the invention to provide a means for radially translating the diametrically disposed detectors relative to the rotation ring. This allows the detectors to be maintained the optimum distance away from the patient while a rotational SPECT scan is being conducted. The detectors may be radially translated simultaneously with their rotation. For example, when a patient is lying on his or her back the patient's body width is greater than his or her body height. As the detectors are rotated their radial motion allows them to follow the contours of the patient's body thereby acquiring the most accurate data.

The scintillation cameras used with the invention are of a type commercially available such as that disclosed in U.S. Pat. No. 4,523,091 issued on Jun. 11, 1985 to Persky which is hereby specifically incorporated by reference.

The gantry and pallet assembly are configured so that if a particular imaging procedure does not require a patient to be supine the pallet can be removed from the support devices and the detectors oriented to a position where the patient could stand or sit between them. This procedure cannot be adopted for rotational SPECT scanning but it is commonly used for spot scanning where the rotation ring has one or two detectors rigidly connected thereto.

DETAILED DESCRIPTION OF THE PREFERRED EMBODIMENT

Figure 1:
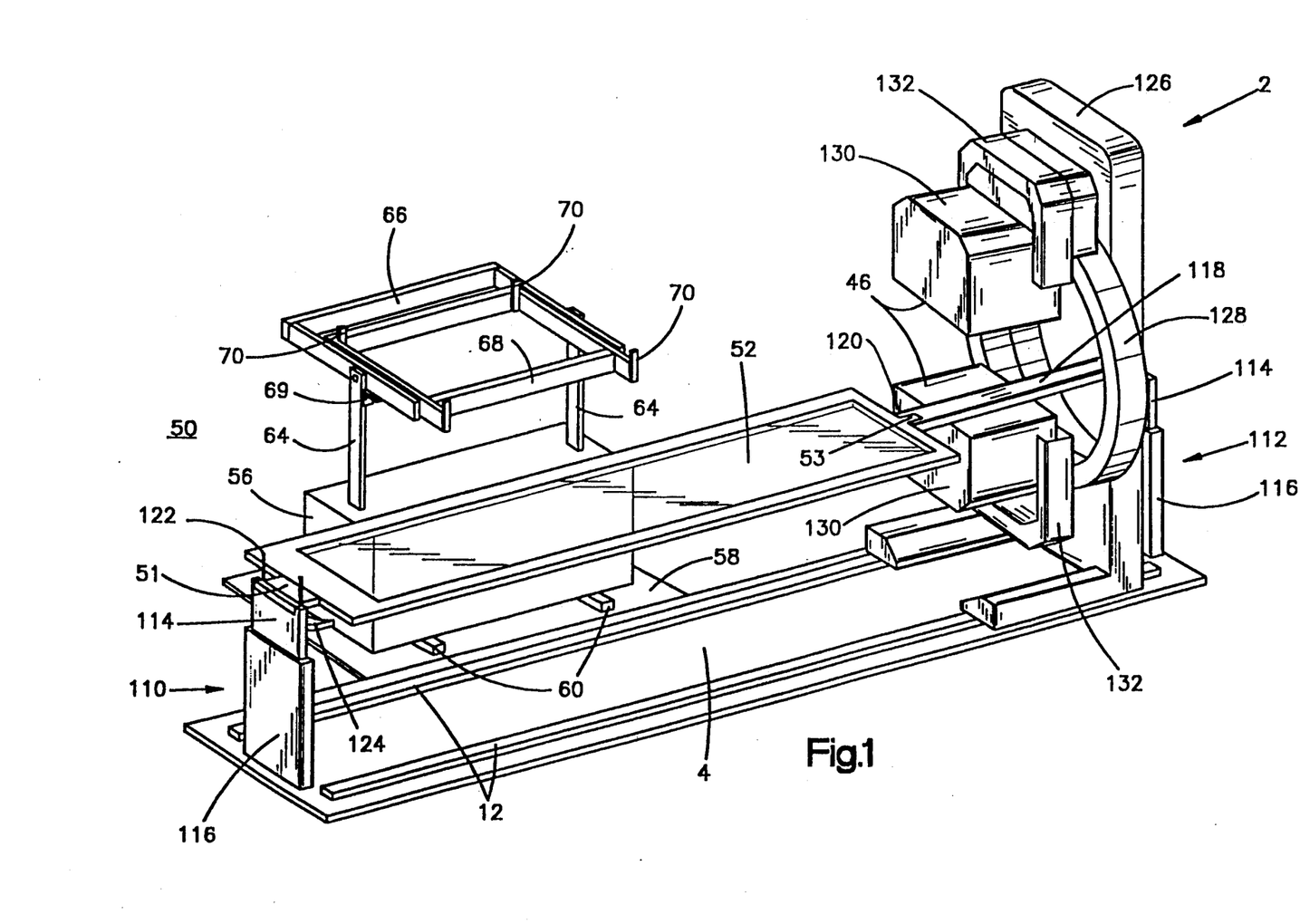
FIG. 1 is a perspective view of the gantry and that part of the pallet assembly used for supporting and transferring the rectangular pallet; the rectangular pallet is shown in position for scanning to be conducted.
Figure 7A:
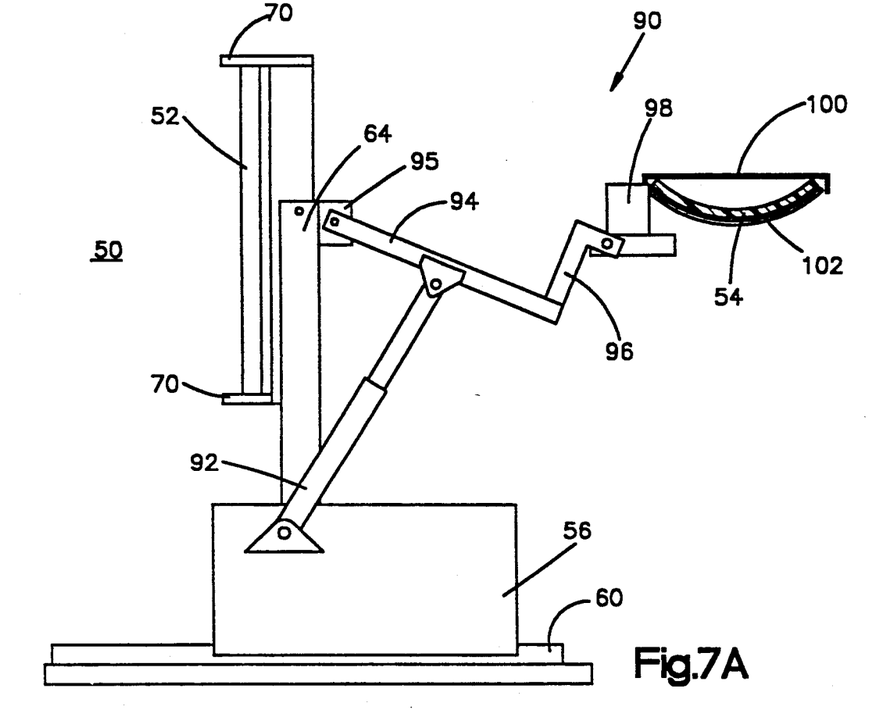
FIG. 7A is an end view of the pallet assembly with the arcuate pallet rack assembly in an extended position.
Figure 7B:
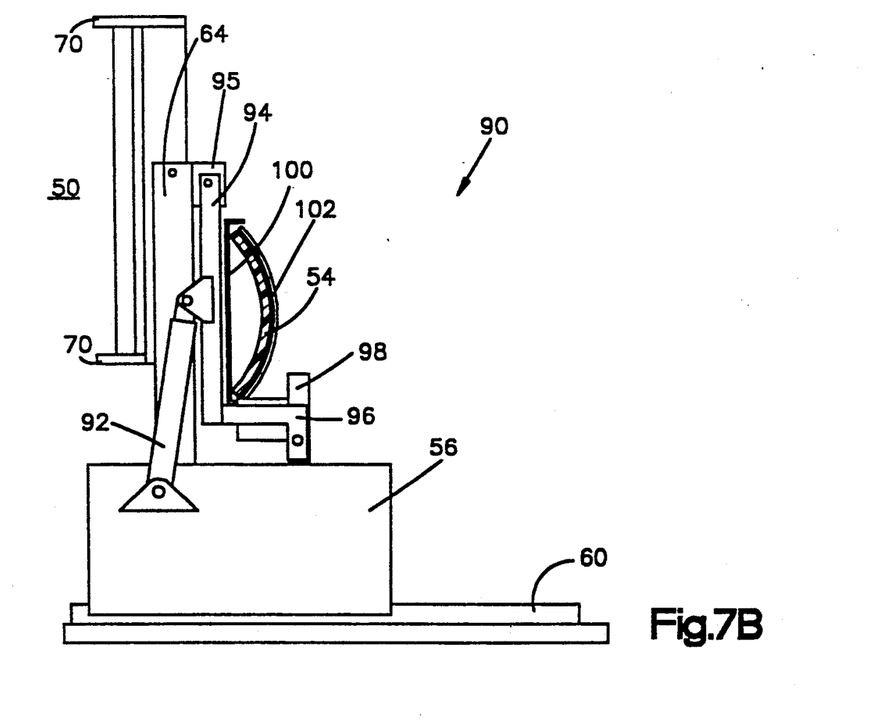
FIG. 7B is an end view of the pallet assembly with the arcuate pallet rack assembly in a retracted position.

Referring now to the drawings and in particular to FIG. 1, there is shown the gantry 2 and that part of the pallet assembly used for storing and transferring the pallet 52. The pallet assembly includes the storage carriage 50, the front pallet support 110 and the rear pallet support 112. The storage carriage 50 is shown in FIGS. 7A and 7B to also include an arcuate pallet rack assembly generally referred to by reference numeral 90. FIG. 7A shows the rack assembly 90 in an extended position and FIG. 7B shows it in a retracted position. The operation of the rack assembly 90 will be more fully described hereinafter.

Figure 6:
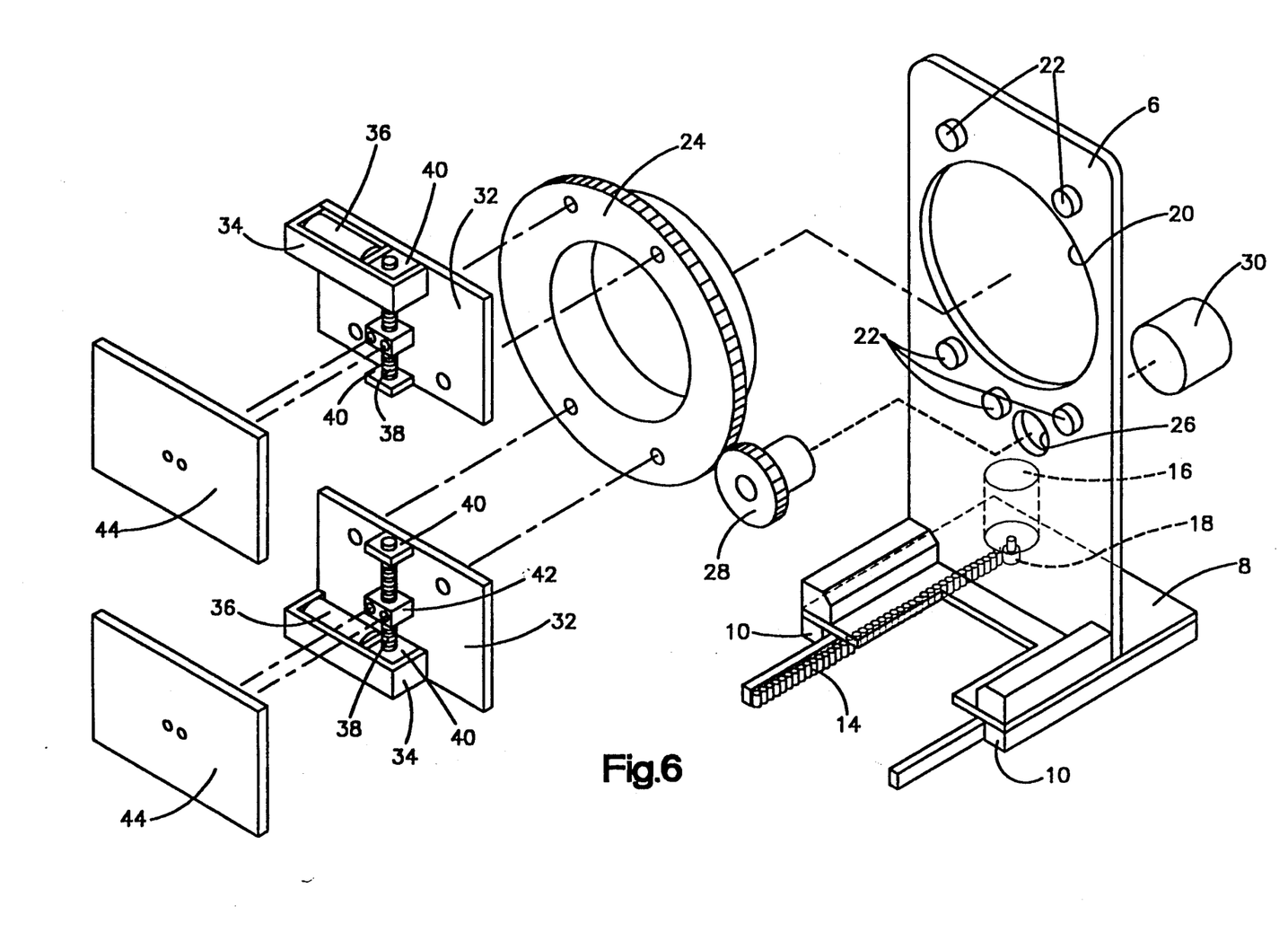
FIG. 6 is an exploded view of the means for rotating the rotation ring, means for translating the gantry, and means for radially translating the detectors.

Referring to FIGS. 1 and 6, the structure of the gantry 2 is clearly shown positioned on the gantry support platform 4. An upright gantry plate 6 is rigidly connected perpendicular to the gantry base 8 in any conventional manner. The gantry base 8 has a pair of support legs 10 which cooperate with the translation tracks 12 which are connected in a substantially parallel manner to the support platform 4 as shown in FIG. 1. The support legs 10 also act as a cantilevered base which helps the gantry 2 maintain its balance.

The gantry 2 is laterally translated along the support platform 4 by a chain and sprocket arrangement as shown in FIG. 6. Drive chain 14 is connected at each end to the support platform 4 in a taut manner. A driving motor 16 rotationally cooperates with a sprocket 18. The sprocket 18 interacts with the drive chain 14 so that when the driving motor 16 is activated the gantry 2 is moved along the translation tracks 12. The gantry 2 can be translated in either direction along the translation tracks 12.

It is apparent that other arrangements could be utilized to translate the gantry 2. For example, a worm gear spanning the length of the support platform 4 and having a block movingly disposed thereon could be used. The worm gear would be rotationally journalled at each end and the block connected to the gantry 2. When the worm gear is mechanically rotated the block and gantry 2 are translated in either direction along the translation tracks 12. Alternatively, other known arrangements could be used to laterally translate the gantry 2.

Figure 2:
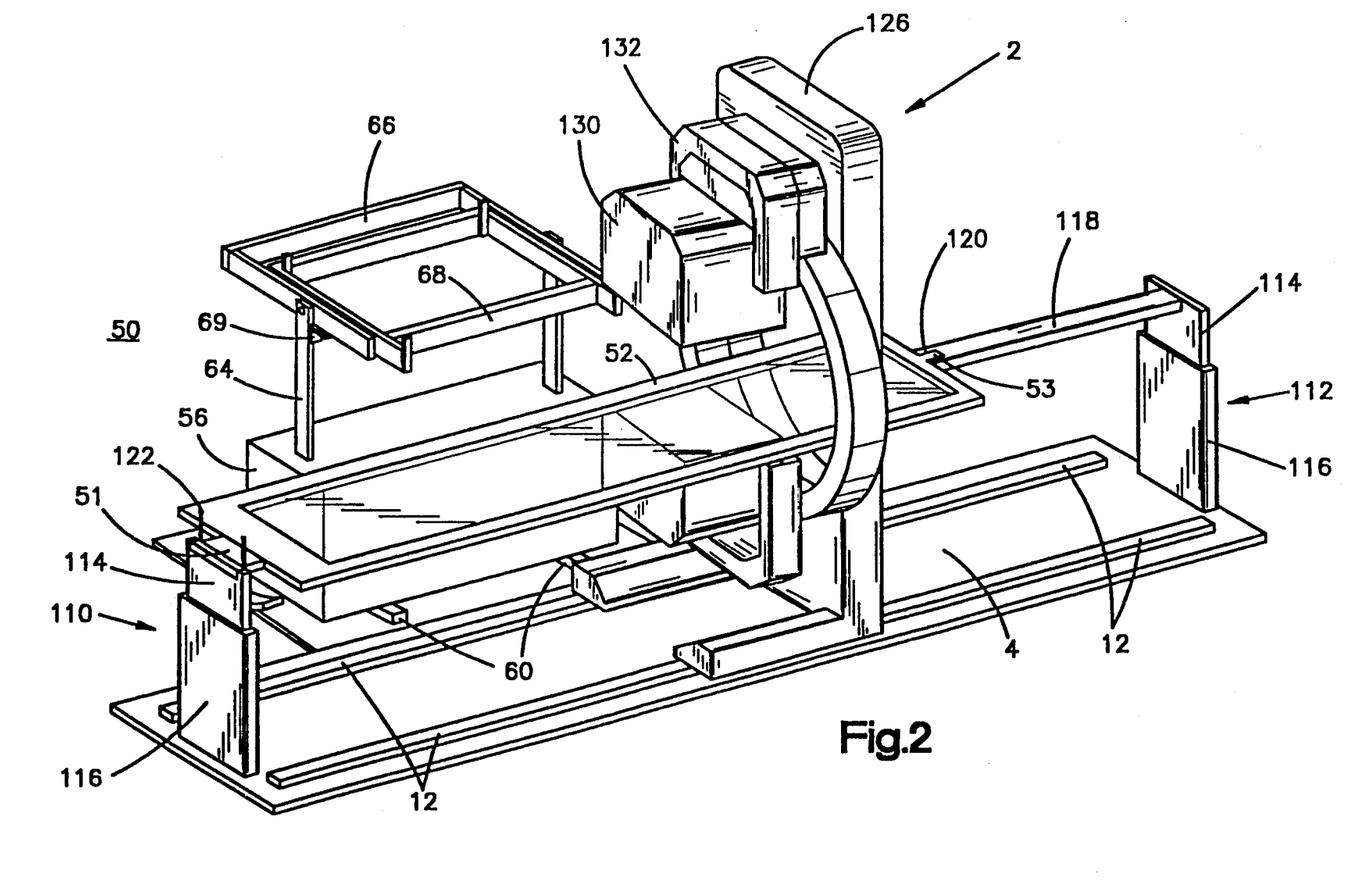
FIG. 2 is a view of FIG. 1 with the gantry translated a distance along the translation tracks.
Figure 4:
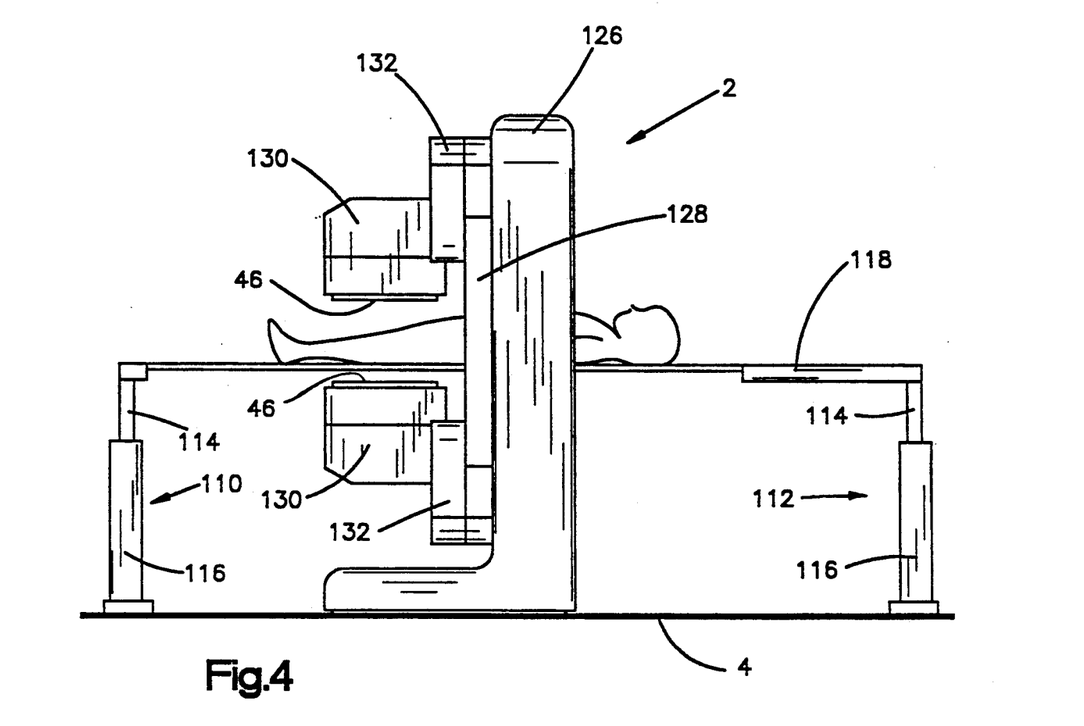
FIG. 4 is a side view of the gantry and pallet assembly with a patient supine on a pallet.

Referring to FIG. 6, the gantry plate 6 has an aperture 20 disposed therein of sufficient diameter so that a patient supported on a pallet can pass longitudinally therethrough. FIG. 4 shows the gantry 2 translated a distance along support platform 4. As the gantry 2 is translated the supine patient supported on the pallet 54 will pass through the aperture 20. The gantry 2 can then be stopped at any point along the axis of the patient's body to conduct the appropriate scan. FIG. 2 also shows the gantry 2 translated a distance along the translation tracks 12. The storage carriage 50 is moved away from the platform 4 so the gantry 2 has ample room to be translated.

The gantry plate 6 has five groove track rollers 22 rigidly connected thereto and configured around the aperture 20 as shown in FIG. 6. The groove track rollers 22 are adapted to rotationally support a rotation ring 24 in any conventional manner. The gantry plate 6 has further disposed therein a spur gear mounting slot 26 into which a spur gear 28 is inserted. The spur gear 28 rotationally cooperates with the rotation ring 24 when both are mounted in position on the gantry plate 6. The spur gear 28 is drivingly connected to a drive motor 30 in a conventional manner so that when the drive motor 30 is activated the rotation of spur gear 28 causes the rotation ring 24 to rotate. It is apparent that other gearing arrangements could be adopted to impart rotation upon the rotation ring 24 which in turn rotates the detectors 46. Other gearing arrangements may utilize alternative approaches without deviating from the scope of the invention.

The rotation ring 24 has two radial back plates 32 rigidly connected thereto in a diametrically opposed manner as shown in FIG. 6. The back plates 32 can be connected to the rotation ring 24 in a known manner, such as nuts and bolts, or they could be permanently anchored to the rotation ring 24. It is preferred they are connected in a removable fashion for maintenance and adjustment purposes. In the preferred embodiment, each back plate 32 has connected thereto a motor mount 34 adapted to contain a drive motor 36. Each drive motor 36 is mechanically coupled in a known manner to a worm gear 38 journalled at each end to worm gear supports 40 which are rigidly connected to the radial back plate 32. Each worm gear 38 has movingly disposed thereon a mounting block 42 to which a detector mounting plate 44 is solidly mounted in a conventional manner. When the drive motors 36 are activated they mechanically drive the worm gears 38 thereby causing the mounting blocks 42 to be radially translated in either direction relative to the rotation ring 24. When the mounting blocks 42 are radially translated the detectors 46 are translated therewith via their coupling to the mounting blocks 42. The drive motor 30 and the drive motors 36 can be simultaneously activated thereby radially translating the detectors 46 simultaneously with the rotation of rotation ring 24. This dual action movement provides optimum results when conducting a rotation SPECT scan.

Referring now to FIG. 1, there is shown a storage carriage, generally referred to by reference numeral 50, which is adapted to support a substantially flat pallet 52 used for whole body scaning and an arcuate pallet 54 used for rotation SPECT scanning. It is important the pallet 52 used for whole body scanning be flat so the detectors can get close to the patients body. The preferred embodiment of the present invention provides a flat pallet which is substantially rectangular. It is apparent that other shapes could be provided without deviating from the scope of the invention.

The storage carriage 50 has a substantially rectangular base 56 movably mounted on a support skid 58. The support skid 58 is substantially perpendicular to the gantry support platform 4 and may be connected to it. The support skid 58 has connected thereto a pair of substantially parallel guide rails 60 that interact with the bottom of the base 56. Thus, the storage carriage 50 can be displaced between a position close to the gantry support platform 4 and a position spaced away from it. When the storage carriage 50 is spaced away from the platform 4 it will not interfere with scanning procedures. The storage carriage 50 may ride on wheels or non-rolling guide means.

Figure 5:
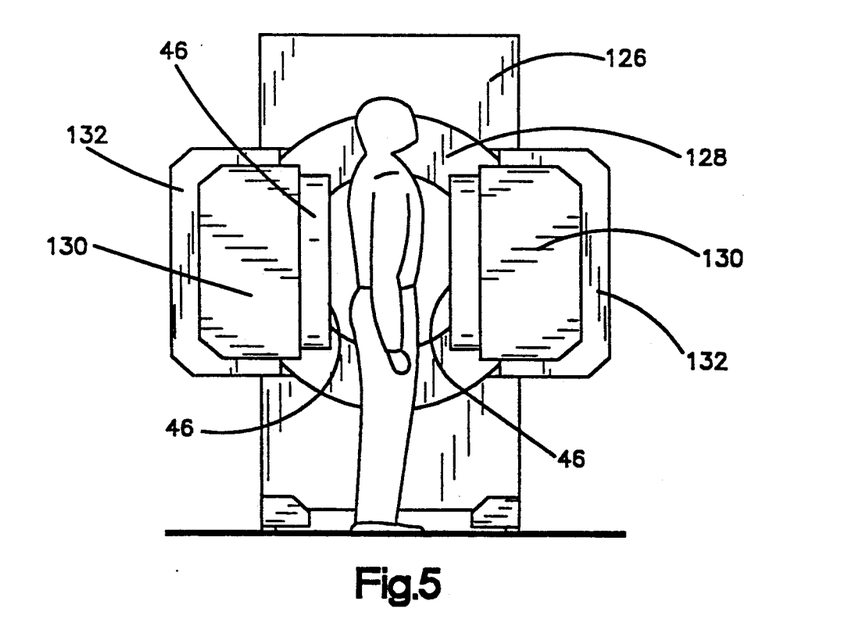
FIG. 5 is a front view of the gantry with a patient standing in position for a scan not requiring the patient to be supine.

Certain scanning procedures are best conducted with the patient standing or sitting. FIG. 5 shows a patient standing with the detectors 46 oriented to conduct a scan. The preferred embodiment of the present invention allows a patient to easily access the detectors 46 in this manner. The patient may stand as shown or sit down if necessary. The detectors 26 extend longitudinally a distance approximately the width of the detector head from the rings. This position minimizes the vibration of the detectors when the ring is moved and further permits the detectors to move to a position in which the patient may stand between the detectors when they are in a horizontal plane. The distance the detectors extend from the ring may vary somewhat, but should be a distance as close to the ring as possible while still permitting the patient to stand between them. The term approximately the width of the detector head would be anywhere from a distance where the camera could fully view the patient to one slightly greater than the width of the head in order to provide for connectors and a full view of the patient.

Figure 1A:
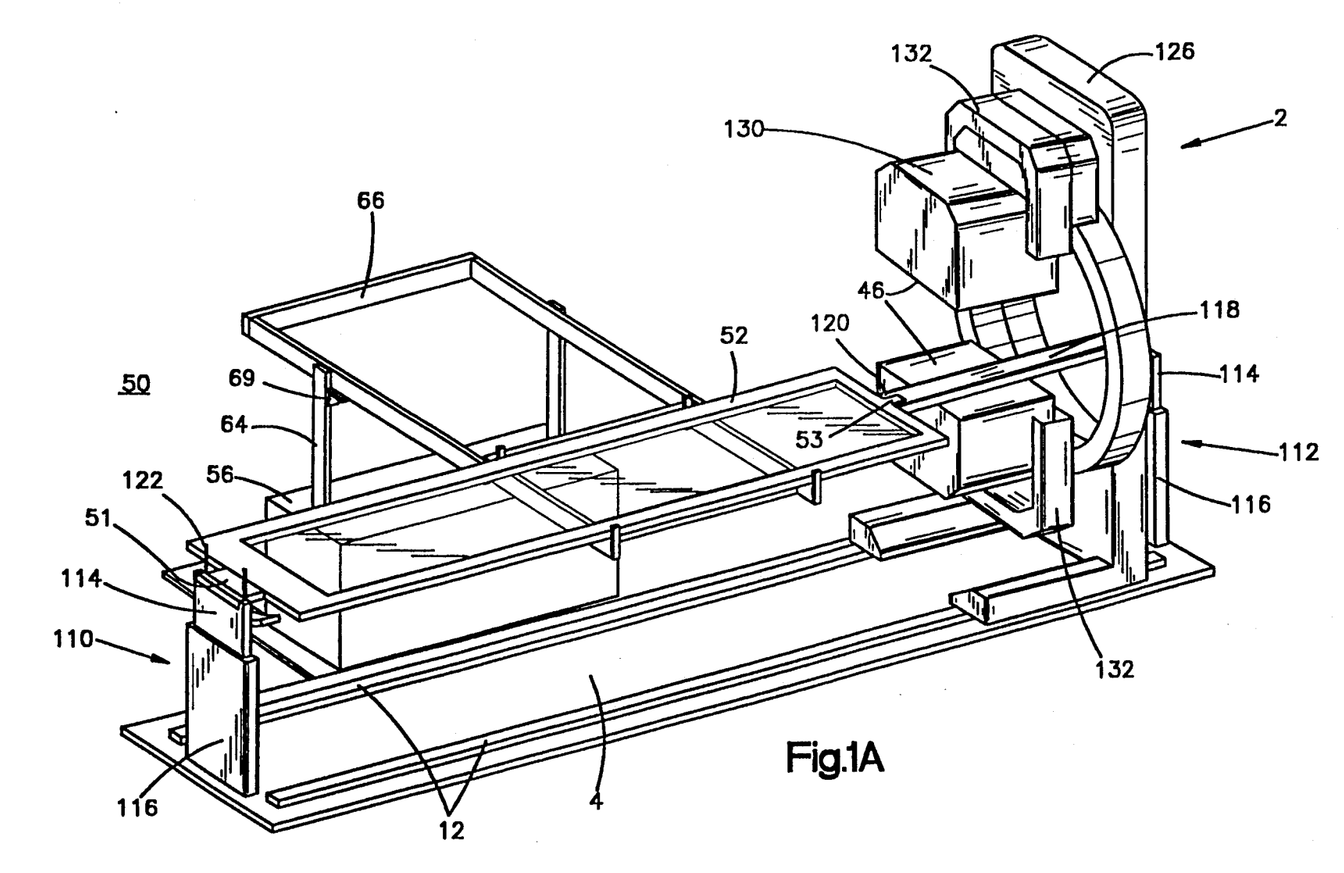
FIG. 1A is a view of FIG. 1 with the frame of the pallet assembly in its fully extended position.
Figure 3:
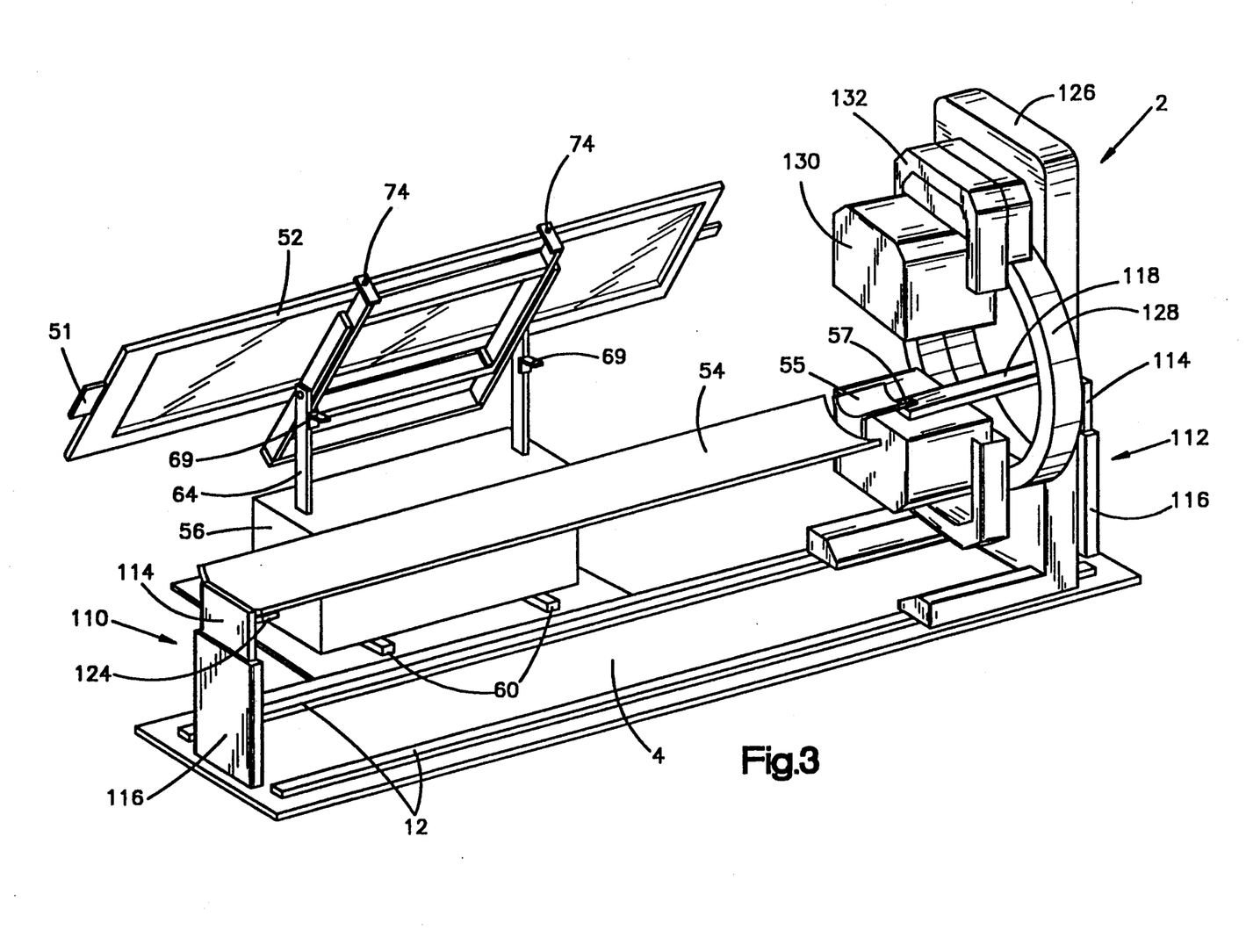
FIG. 3 is a view of FIG. 1 with the rectangular pallet in its storage position and the arcuate pallet in position for scanning.

Referring again to FIG. 1, the base 56 has perpendicularly extending therefrom and connected thereto a pair of vertical frame support posts 64 which pivotally support a frame having an external frame component 66 and an extendable frame component 68. The extendable frame component 68 is slidably contained inside the external frame component 66 so that the extendable component 68 can be moved between an extended position for transferring the rectangular pallet 52, as shown in FIG. 1A, and a retracted position for storing it, as shown in FIG. 3. Each support post 64 has connected thereto a cantilevered buttress 69 which prevents the frame from rotating past horizontal.

The extendable frame component 68 has four pallet retaining pegs 70 extending perpendicularly therefrom and firmly connected thereto. The pegs 70 help guide the pallet 52 into place when being placed on the extendable frame component 68.

Referring to FIG. 1A, to transfer the pallet 52 from the vertically adjustable support means 110, 112 to the storage carriage 50, the pallet 52 is raised so that the extendable frame component 68 can be extended underneath it when the storage carriage 50 is moved close to the platform 4. The support means 110, 112 then lower the pallet 52 onto the extendable frame component 68. The extendable frame component 68 can then be retracted into its storage position as best shown in FIG. 3. The storage carriage 50 can then be moved away from the platform 4 so that other scans can be performed.

The frontmost pegs on the extendable frame component 68 have apertures therein into which a spring loaded detent 74 is inserted to exert pressure against the edge of the pallet 52. Thus, the pallet 52 can be tilted into its storage position which is close to vertical as shown in FIG. 3.

Referring now to FIGS. 7A and 7B, there is shown the storage carriage 50 with an arcuate pallet rack assembly generally referred by reference numeral 90. The rack assembly 90 has a pair of telescoping arms 92 pivotally connected at one end to the base 56. The arms 92 can telescope in any conventional manner. Each arm 92 has pivotally connected near its other end a cross member 94. Each cross member 94 has an L-shaped extension rigidly connected thereto as best seen in FIG. 7A. The other end of each cross member 94 is pivotally connected to a brace 95 mounted on the frame support posts 64. A hinged pallet coupling 98 is pivotally connected to each L-shaped extension 96. The couplings 98 have connected thereto a retaining bracket 100 and a pallet support brace 102. The retaining brackets 100 and the support braces 102 are adapted to firmly grasp therebetween the arcuate pallet 54 for storing and transferring as shown in FIGS. 7A and 7B.

The rack assembly 90 is used to displace the arcuate pallet 54 between a storage position shown in FIG. 7B, and a transfer position as shown in FIG. 7A. When the arcuate pallet 54 is in the transfer position the retaining brackets 100 are pivoted so that the arcuate pallet 54 can be lifted off the arcuate pallet support braces 102. Thus, the pallet 54 can be transferred onto the pallet support means 110, 112 for rotational SPECT scanning.

Referring now to FIG. 1, 1A, and 3 either pallet 52, or arcuate pallet 54 can be detachably supported on front pallet support 110 and rear pallet support 112 for use when scans are being performed. Both the front and rear pallet supports 110, 112 are vertically adjustable so that a pallet placed thereon can be moved up and down thereby achieving the proper spatial relationship between a patient and the detectors 46 when conducting a scan. Each pallet support 110, 112 has a vertically extendable component 114 which is movably contained within a pallet support housing 116. The extendable components 114 can be controlled in any conventional manner so they telescope relative to the support housings 116. The preferred method of control is a worm gear arrangement which provides for precise adjustments.

The rear pallet support 112 has a cantilevered arm 118 extending perpendicularly therefrom. The cantilevered arm 118 has a notch 120 formed therein into which one end of either pallet is detachably supported. The pallet 52 has a support peg 53 connected to one end which firmly fits within the notch 120. The other end of the pallet 52 has a support flange 51. The support flange 51 cooperates with a retaining bar 122 which is mounted on the vertically extendable component 114 of the front pallet support 110. When the support flange 51 is placed within the retaining bar 122, and the support peg 53 is placed within the notch 120, the pallet 52 is firmly held in place for scanning purposes.

Similarly, the arcuate pallet 54 has connected at one end a head rest 55. The head rest 55 has connected thereto a support peg 57. The support peg 57 firmly fits within the notch 120. The other end of the arcuate pallet 54 rests upon an arcuate ledge 124 connected to the vertically extendable component 114 of the front pallet support 110. When the support peg 57 is placed within the notch 120, and the other end of the arcuate pallet 54 is placed upon the arcuate ledge 124, the arcuate pallet 54 is firmly held in place for scanning purposes as best shown in FIG. 3.

The internal structure of the gantry 2 is protected by a gantry plate cover 126 as are other components of the preferred embodiment of the invention. The rotation ring 24 has a cover 128 placed thereover which snugly cooperates with the cover 126. The detectors 46 have covers 130 protecting them and covers 132 are placed over the mechanisms which radially translate the detectors. The covers 126, 128, 130, and 132 prevent dirt and other particles from fouling the operations of the machinery and are aesthetically appealing.

While the preferred embodiment of the invention has been shown and described in detail, it is recognized that various modifications and rearrangements may be resorted to without departing from the scope of the invention as defined in the claims.

We claim:

1. A gantry and pallet assembly used in nuclear imaging, comprising:
    a gantry having a rotation ring that defines an aperture within which a patient may pass during a scan, said rotation ring also defining a longitudinal axis when laterally translated;
    two diametrically substantially identical disposed detectors rigidly connected to and in close proximity to but extending longitudinally a distance approximately the width of the detectors from said ring to minimize vibration of the detectors when said ring is moved;
    means for radially translating the detectors on the ring so that the detectors may move radially relative to a patient and the longitudinal axis;
    means for rotating said ring so that said detectors are rotated thereby acquiring data used for mapping the distribution of radioactively tagged pharmaceutical previously injected into a patient's body, the means for rotating said ring having at least one position wherein the disposed detectors are in a horizontal plane so that a patient may be positioned between them in a standing position when no pallet is present;
    a first pallet supported at each end by a supporting means so that said first pallet is substantially coaxial with said longitudinal axis, said pallet positioned so that it is easily accessible to a patient getting onto or off of it;
    means for laterally translating said gantry along a translational track supported along its length so that said detectors pass over the patient's body supported on said first pallet thereby acquiring data from diametrical areas of the patient's body used for mapping the distribution of radioactively tagged pharmaceutical previously injected into the patient's body, the patient's body passing at least partially within said aperture when said gantry is translated along said translational track.

2. A gantry and pallet asembly used in nuclear imaging as recited in claim 1 wherein said first pallet is positioned so that one end is adjacent said at least one detector when said gantry is in one position so that said at least one detector can acquire data from a patient's head region when lying on said pallet, the data being used for mapping the distribution of at least one radioactively tagged pharmaceutical previously injected into the patient's body.

3. A gantry and pallet assembly used in nuclear imaging as recited in claim 2, wherein each of said supporting means are vertically adjustable so that the spatial relationship of said pallet to said at least one detector can be adjusted thereby moving a patient supported by said pallet closer to or further away from either of said at least one detector to achieve the desired positioning of the patient to perform a particular imaging procedure, said rotation ring capable of being incrementally rotated.

4. A gantry and pallet assembly used in nuclear imaging as recited in claim 3, wherein said first pallet is substantially rectangular and flat and used for whole body scanning whereby said gantry is laterally translated along said guide means causing said first pallet to pass longitudinally through said aperture, said first pallet being detachably supported at each end to one of said supporting means.

5. A gantry and pallet assembly used in nuclear imaging as recited in claim 4 wherein said first pallet is interchangeable with a second pallet which is substantially arcuate and used for rotational SPECT scanning whereby said at least one detector are positioned over an area of interest of the patient's body then rotated thereby acquiring a sufficient amount of data to map the distribution of at least one radioactively tagged pharmaceutical previously introduced into the patient's body, said second pallet being detachably supported by each of said supporting means, said first and said second pallets being storable on a storage carriage positioned in close proximity to said gantry, said storage carriage having a frame mounted above a base and adapted to retain said first pallet, said frame having an extendable frame component which can be positioned so that said first pallet can be easily removed therefrom or placed thereon.

6. A gantry and pallet assembly used in nuclear imaging as recited in claim 5 wherein said storage carriage further comprises a pair of frame support posts extending from said base, said extendable frame component being pivotally mounted to said posts, each of said posts having a cantilever buttress connected thereto for preventing said frame from pivoting past horizontal in one direction, said extendable frame component having four pallet retaining pegs extending therefrom for retaining said first pallet, two of said pegs each having an aperture therein into which a spring loaded detent is inserted for exerting pressure against said first pallet when positioned on said frame thereby holding said first pallet firmly within said frame.

7. A gantry and pallet assembly used in nuclear imaging as recited in claim 5 wherein said extendable frame component is slidably mounted inside an external frame component so that said extendable frame component can be positioned between a storage position and a position where said first pallet can be easily removed therefrom or placed thereon, said storage carriage being movably positioned substantially parallel to said longitudinal axis so that said storage carriage can be positioned close to said gantry for transferring said pallets from said storage carriage to said supporting means or from said supporting means to said storage carriage, or away from said gantry so it doesn't interfere with the scanning procedures.

8. A gantry and pallet assembly used in nuclear imaging as recited in claim 5 further comprising means for displacing said arcuate pallet between a retracted position and a position where said arcuate pallet can be easily transferred to or from said support means.

9. A gantry and pallet assembly used in nuclear imaging as recited in claim 8 wherein said displacing means comprises a pair of telescoping arms pivotally connected to said base in a substantially parallel manner, said telescoping arms having connected thereto means for grasping said arcuate pallet and moving it between a position where said arcuate pallet can be easily transferred to or from said support means, and a position where said arcuate pallet is stored in close proximity to said frame support posts.

10. A gantry and pallet assembly used in nuclear imaging as recited in claim 5 wherein said guide means comprises a pair of substantially parallel translation tracks mounted on a gantry support platform so that said gantry can be translated along said translation tracks.

11. A gantry and pallet assembly used in nuclear imaging as recited in claim 1, wherein said gantry comprises a gantry plate having a second aperture disposed therein so that either of said pallets can pass through said second aperture when said gantry is translated along said guide means, said gantry plate being perpendicularly connected to a gantry base having at least one support leg extending therefrom, said rotation ring rotationally disposed on said gantry plate coaxial with said aperture.

12. A gantry and pallet assembly used in nuelear imaging as recited in claim 11 wherein said gantry plate has perpedicularly connected thereto a plurality of groove track rollers adapted to cooperate with said rotation ring for rotationally guiding said rotation ring, said means for rotating said rotation ring comprises a first driving motor rotationally connected to a spur gear which rotationally cooperates with said rotation ring, said spur gear supported in a slot disposed in said gantry plate.

13. A gantry and pallet assembly used in nuclear imaging as recited in claim 11, wherein said means for laterally translating said gantry comprises a second driving motor having a sprocket rotationally connected thereto, said driving motor and sprocket connected to said gantry base, a drive chain which engagingly cooperates with said sprocket, said drive chain connected at each end to said support platform so that when said second driving motor is activated said sprocket cooperates with said driving chain thereby translating said gantry along a pair of translation tracks which are substantially parallel to a longitudinal axis of said rotation ring.

14. A gantry and pallet assembly used in nuclear imaging as recited in claim 1 further comprising a pair of radial back plates connected to said rotation ring, each of said back plates having movingly connected thereto a detector mounting plate, said means for radially translating each of said at least one detector comprises a worm gear journalled at each end to a worm gear support connected to said back plate, said worm gear having a mounting block movingly disposed thereon to which said at least one detector mounting plate is connected, and a driving motor for cooperating with said worm gear so that said at least one detector are radially translated relative to said ring.

15. A gantry and pallet assembly used in nuclear imaging as recited in claim 14 wherein each of said back plates further comprises a motor mount to which said driving motor is mounted, said means for translating each of said detectors being disposed between said radial back plate and said at least one detector mounting plate.

16. A pallet assembly, comprising:
a substantially rectangular and flat pallet upon which a patient will lie for having a whole body scan performed by a nuclear imaging gantry assembly;
means for supporting said pallet at each end thereby immobilizing said pallet in a desired position for performing the whole body scan;
a storage carriage adapted to retain said pallet, said storage carriage comprising a frame, a support platform for supporting said frame above a base, said frame having an extendable frame component capable of being displaced between a fully extended position and a fully retracted position;
means for translating said storage carriage perpendicular to said support platform between an unloading position and a storage position so that when said storage carriage is in said unloading position and said extendable frame component is fully extended said rectangular pallet can be easily transferred between said frame and said pallet supporting means.

17. A pallet assembly as recited in claim 16, further comprising a substantially arcuate pallet upon which a patient will lie for having a rotational SPECT scan performed by said nuclear imaging gantry assembly, said arcuate pallet having at each end means for being detachably connected to said pallet supporting means.

18. A pallet assembly as recited in claim 17, wherein said frame further comprises an external frame component, said extendable frame component slidably mounted inside said external frame component, said frame supporting means comprising a pair of frame support posts extending from said base and pivotally supporting said external frame component so that said frame can be pivoted between horizontal and a position therefrom.

19. A pallet assembly as recited in claim 18 wherein each of said frame support posts has a cantilevered buttress connected thereto for preventing said frame from pivoting past horizontal in one direction, said base having at least two support clips adapted to retain said arcuate pallet for storage purposes, said extendable frame component having four pallet retaining pegs extending therefrom for retaining said first pallet, two of said pegs each having an aperture therein into which a spring loaded detent is inserted for exerting pressure against said first pallet when positioned on said frame thereby holding said first pallet firmly within said frame.

20. A pallet assembly as recited in claim 17, wherein said pallet supporting means comprises a front pallet support and a rear pallet support both being vertically disposed on a gantry support platform, said rear pallet support having a cantilevered arm extending perpendicularly therefrom for supporting one end of either of said pallets, both said front pallet support and said rear pallet support being vertically adjustable so that when one of said pallets is placed thereon it can be moved vertically to a position for performing the appropriate scan.

21. A pallet assembly as recited in claim 20 wherein both said front pallet support and said rear pallet support have a vertically extendable component contained within a pallet support housing connected to said gantry support platform, said vertically extendable components capable of raising and lowering said rectangular pallet.

22. A pallet assembly as recited in claim 17, and further comprising means for displacing said arcuate pallet between a retracted position and a position where said arcuate pallet can be easily transferred to or from said support means.

23. A pallet assembly as recited in claim 22, wherein said displacing means comprises a pair of arms mounted to said base in a substantially parallel manner, said arms having connected thereto means for moving said arcuate pallet between a position where said arcuate pallet can be easily transferred to or from said support means, and a position where said arcuate pallet is stored in close proximity to said frame support posts.

24. A pallet assembly as recited in claim 23, wherein said arms are telescoping and pivotally mounted to said base.

25. A pallet assembly as recited in claim 23, wherein said means for moving said arcuate pallet comprises a pair of cross members each pivotally mounted to one of said arms, one end of each of said cross members pivotally connected to said frame support posts, said cross members having pivotally connected thereto a pallet coupling, each of said pallet couplings having connected thereto means for grasping said arcuate pallet so that said arcuate pallet can be moved between a position where it can easily be transferred to said support means, and a position where said arcuate pallet rests upon said cross members.

26. A gantry assembly used in nuclear imaging, comprising:
a gantry having a rotation ring rotationally disposed thereon, said rotation ring defining an aperture through which a patient may pass during a scan;
at least one detector connected in a generally rigid manner and in close proximity to but extending longitudinally a distance approximately the width of the at least one detector from said rotation ring to minimize vibration of the at least one detector when said rotation ring is moved;
means for rotating said rotation ring so that said at least one detector is rotated thereby acquiring data used for mapping the distribution of at least one radioactively tagged pharmaceutical previously injected into a patient's body the means for rotating said ring having at least one position wherein the at least one detector is in a horizontal facing position so that a patient may be viewed in a standing position when no pallet is present;
means for laterally translating said gantry along a translational track whereby said detector passes over the patient's body supported on a pallet thereby acquiring data from diametrical areas of the patient's body used in conducting a whole body scan;
means for radially translating said at least one detector relative to said rotation ring so that said at least one detector capable of being radially translated can be moved relative to the patient thereby providing optimum positioning of said at least one detector capable of being radially translated during performance of a scan.

27. A gantry assembly used in nuclear imaging as recited in claim 26 wherein a pair of substantially parallel translation tracks mounted on a gantry support platform so that said gantry can be translated along said translation tracks, said rotation ring capable of being incrementally rotated.

28. A gantry assembly used in nuclear imaging as recited in claim 26, wherein there are at least two opposed detectors and said gantry comprises a gantry plate having a second aperture disposed therein so that the pallet can pass through said second aperture when said gantry is translated along said translational track, said gantry plate being perpendiculary connected to a gantry base having at least one support leg extending therefrom, said rotation ring rotationally disposed on said gantry plate coaxial with said aperture.

29. A gantry assembly used in nuclear imaging as recited in claim 28 wherein said gantry plate has perpendicularly connected thereto a plurality of groove track rollers adapted to cooperate with said rotation ring for rotationally guiding said ring.

30. A gantry assembly used in nuclear imaging as recited in claim 28 wherein said means for rotating said rotation ring comprises a first driving motor rotationally connected to a spur gear which rotationally cooperates with said rotation ring, said spur gear supported in a slot disposed in said gantry plate.

31. A gantry assembly used in nuclear imaging as recited in claim 30 wherein said means for laterally translating said gantry comprises a second driving motor having a sprocket rotationally connected thereto, said driving motor and sprocket connected to said gantry base, a drive chain which engagingly cooperates with said sprocket, said drive chain connected at each end to said support platform so that when said second driving motor is activated said sprocket cooperates with said driving chain thereby translating said gantry along a pair of translation tracks which are substantially parallel to a longitudinal axis of said rotation ring.

32. A gantry assembly used in nuclear imaging as recited in claim 18 further comprising a pair of radial back plates connected to said rotation ring, each of said back plates having movingly connected thereto a detector mounting plate, said means for radially translating each of said detectors comprises a worm gear journalled at each end to a worm gear support connected to said back plate, said worm gear having a mounting block movingly disposed thereon to which said at least one detector mounting plate is connected, and a driving motor for cooperating with said worm gear so that said at least one detector are radially translated relative to said ring.

33. A gantry assembly used in nuclear imaging as recited in claim 32 wherein each of said back plates further comprises a motor mount to which said driving motor is mounted, said means for translating each of said at least one detector is disposed between said radial back plate and said at least one detector mounting plate.

* * * * *